United States Patent [19]

Sarge III et al.

[11] 4,210,144
[45] Jul. 1, 1980

[54] DISPOSABLE DIAPER HAVING REFASTENABLE TAPE SYSTEM

[75] Inventors: Henry D. Sarge III, Okeana; Alan R. Spector, Cincinnati, both of Ohio

[73] Assignee: The Procter & Gamble Company, Cincinnati, Ohio

[21] Appl. No.: 943,595

[22] Filed: Sep. 18, 1978

[51] Int. Cl.² .............................................. A61F 13/16
[52] U.S. Cl. .............................. 128/287; 128/DIG. 30
[58] Field of Search .................... 128/284, 287, 290 R, 128/290 W, DIG. 30

[56] References Cited

U.S. PATENT DOCUMENTS

| | | | |
|---|---|---|---|
| 3,561,446 | 2/1971 | Jones, Sr. | 128/287 |
| 3,636,952 | 1/1972 | George | 128/287 |
| 3,783,871 | 1/1974 | Sabee | 128/287 |
| 3,867,940 | 2/1975 | Mesek et al. | 128/287 |
| 3,952,745 | 4/1976 | Duncan | 128/287 |
| 4,055,182 | 10/1977 | Mach | 128/287 |
| 4,055,183 | 10/1977 | Ryan et al. | 128/287 |
| 4,058,125 | 11/1977 | Ness | 128/287 |
| 4,067,337 | 1/1978 | Ness | 128/287 |

Primary Examiner—C. Fred Rosenbaum
Attorney, Agent, or Firm—Thomas J. Slone; Fredrick H. Braun; Richard C. Witte

[57] ABSTRACT

An improved disposable diaper of the type having a relatively high elongation to tensile force property, an absorbent pad, and tape-tab fasteners coated with a peelable adhesive. The backsheet is reinforced by coating the mother's bond region thereof with a material having high tensile strength and a low elongation to tensile force property relative to the backsheet material. The coating may be continuous or patterned and may be disposed on either the outwardly facing surface or the inwardly facing surface of the mother's bond region of the backsheet. When applied to the inwardly facing surface, the coating material may be adhesive material and may secure the backsheet to the pad assembly of the diaper. The reinforcement of the backsheet improves the resistance of the backsheet to stretching and tearing when subjected to tensile forces during fastening and wearing, and to peeling forces when the tape-tab fasteners are being peeled open. Thus, the fasteners are refastenable.

19 Claims, 6 Drawing Figures

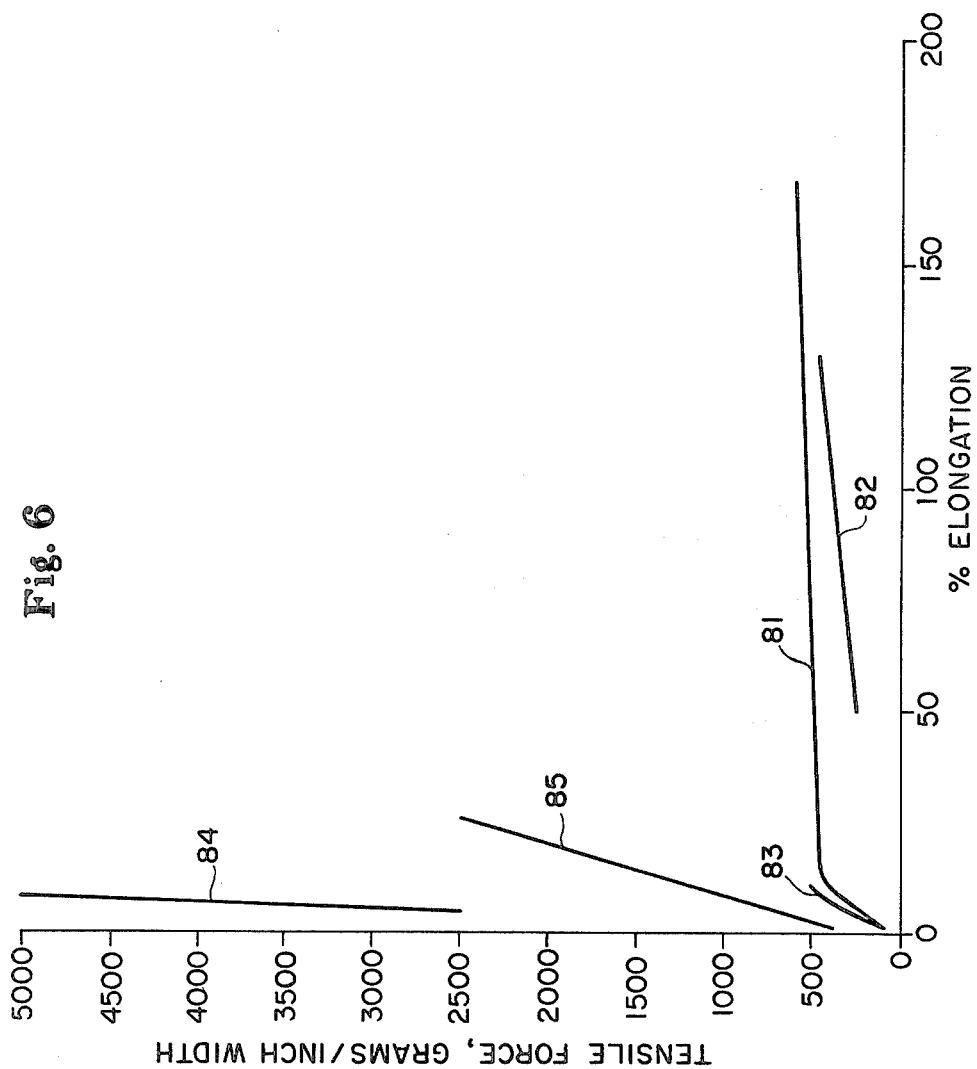

DISPOSABLE DIAPER HAVING REFASTENABLE TAPE SYSTEM

DESCRIPTION

1. Technical Field

This invention relates to disposable diapers having high-strength tape-tab fasteners and which diapers are so constructed that at least one tape tab can be released and securely refastened. This provides non-destructive means for enabling inspection of a diaper being worn to ascertain the need for changing the diaper without precipitating a need to change the diaper if discovered to not be soiled.

2. Background Art

A disposable diaper of the general type to which the present invention pertains is disclosed and described as a preferred embodiment in U.S. Pat. No. 3,952,745 which issued Apr. 27, 1976 to Robert C. Duncan, and shown in FIGS. 1 through 3 thereof. In that construction, top and bottom end edge portions of a liquid pervious topsheet are U-folded and disposed in juxtaposed relation to transverse end portions of a moisture impervious backsheet. One transverse glue bead secures each juxtaposed pair of end edge portions together; reference glue beads 17 and 18, FIG. 2. Additionally, that diaper construction comprises a wet-strength back tissue sheet 2 in juxtaposed relation with the backsheet. Each end portion of the back tissue sheet is secured to the backsheet by a transverse glue bead; reference glue beads 11 and 12, FIG. 2. That diaper construction still further comprises tape-tab fasteners designated 13 and 14 which each have one end that is factory-secured or anchored to a corner of the back portion of the diaper. The opposite ends of such tape-tab fasteners are commonly referred to as the mother's bond ends and will be so referred to hereinafter. Essentially, glue beads 11, 12, 17 and 18 are provided to effect structural integrity of the diaper, and improved disposability. That is, to secure the members of the diaper together so that the diaper is sufficiently strong to render it suitable for its intended purpose, and to render it sufficiently strippable to conveniently subject its absorbent core material to hydraulic erosion in, for instance, a flushing toilet.

U.S. Pat. No. 3,867,940 which issued Feb. 25, 1975 to Frederick K. Mesek et al. discloses a Scrim Reinforced Disposable Diaper having tape-tab fasteners wherein scrim is provided to prevent stretching and rupture of the backsheet due to tension in the tabs generated during diapering, wearing, and removal. The reinforced areas may include the areas of the backsheet to which the factory bonds are made as well as the areas to which the mother's bonds are made. The latter areas are hereinafter referred to as mother's bond regions.

U.S. Pat. No. 4,055,182 which issued Oct. 25, 1977 to Robert John Mack discloses a Disposable Diaper Reinforcement wherein areas of the backsheet to which the factory bonded ends of tape-tab fasteners are secured are reinforced by adhesive means intermediate the backsheet and adjacent pad structure. The adhesive means is expressly stated to extend beyond the areas of tape-tab bonding per se.

U.S. Pat. No. 4,055,183 which issued Oct. 25, 1977 to Arthur Sensor Ryan et al. discloses a Disposable Diaper With Cutout Pad At Tape Attachment Area so that forces exerted on the free ends of the fastening tapes are better distributed to the backsheet and the topsheet of the diaper.

U.S. Pat. No. 4,058,125 which issued Nov. 15, 1977 and U.S. Pat. No. 4,067,337 which issued Jan. 10, 1978, both to Irving S. Ness, disclose tape-tab systems comprising, for example, open mesh scrim adhesively secured to each tape tab's adhesive surface in order to achieve stress distribution, and peelability/refastenability, respectively.

As compared to the background art, the present invention provides improved mother's bond tape-tab strength and release/refastenability through the use of structural materials, coatings and adhesives having predetermined relative strength relations without having to provide additional structural members per se and without having to cut-out or otherwise modify the configuration of the diaper pad or other structural members of the diaper.

DISCLOSURE OF THE INVENTION

In accordance with one aspect of the present invention, there is provided an improved disposable diaper of the type having a substantially moisture-impervious backsheet of relatively thin material having a relatively high elongation to tensile force property, a pad assembly, and a plurality of tape-tab fasteners having free ends which are coated on one surface with a peelable first adhesive so that the free ends can be adhesively secured to an outwardly facing mother's bond region of the backsheet when the diaper is applied to a user. The improvement comprises coating a predetermined portion of a surface of the backsheet in the mother's bond region thereof with a material having relatively high tensile strength and a relatively low elongation to tensile force property whereby mother's bonds will have increased tensile strength and improved tape-tab peelability/refastenability. Preferably the coated surface is the inwardly facing surface of the backsheet. The improvement may further comprise having a predetermined surface portion of a flexible member of the pad assembly juxtaposed in face-to-face relation with the inwardly facing surface of the mother's bond region of the backsheet, the predetermined surface portion of the flexible member and the juxtaposed surface of the mother's bond region of the backsheet being adhesively secured together by a coating comprising a pattern of a second adhesive disposed therebetween and defining a plurality of spaced unsupported segments of the backsheet, the first adhesive having a peel strength greater than the tensile yield strength of unsupported backsheet material, and the second adhesive having a substantially greater tensile strength than the peel strength of the first adhesive. The flexible member may be a moisture pervious topsheet or a back tissue sheet or both. The coating material, and then pattern of the second adhesive may be parallel glue beads which extend transverse the portion of the diaper comprising the mother's bond region. The composite surface area of the pattern of the second adhesive is at least about five percent of the surface area of the mother's bond region, and is preferably about five to twenty-five percent thereof, and must preferably from about ten to about fifteen percent thereof.

BRIEF DESCRIPTION OF THE DRAWINGS

While the claims hereof particularly point out and distinctly claim the subject matter of the present invention, it is believed the invention will be better understood in view of the following detailed description of the invention taken in conjunction with the accompanying drawings in which corresponding features of the several views are identically designated, and in which:

FIG. 6 is a graph showing elongation to tensile force property data for selected materials and combinations of materials which are suitable for inclusion in disposable diaper embodiments of the present invention.

DETAILED DESCRIPTION OF THE INVENTION

Figure 1:
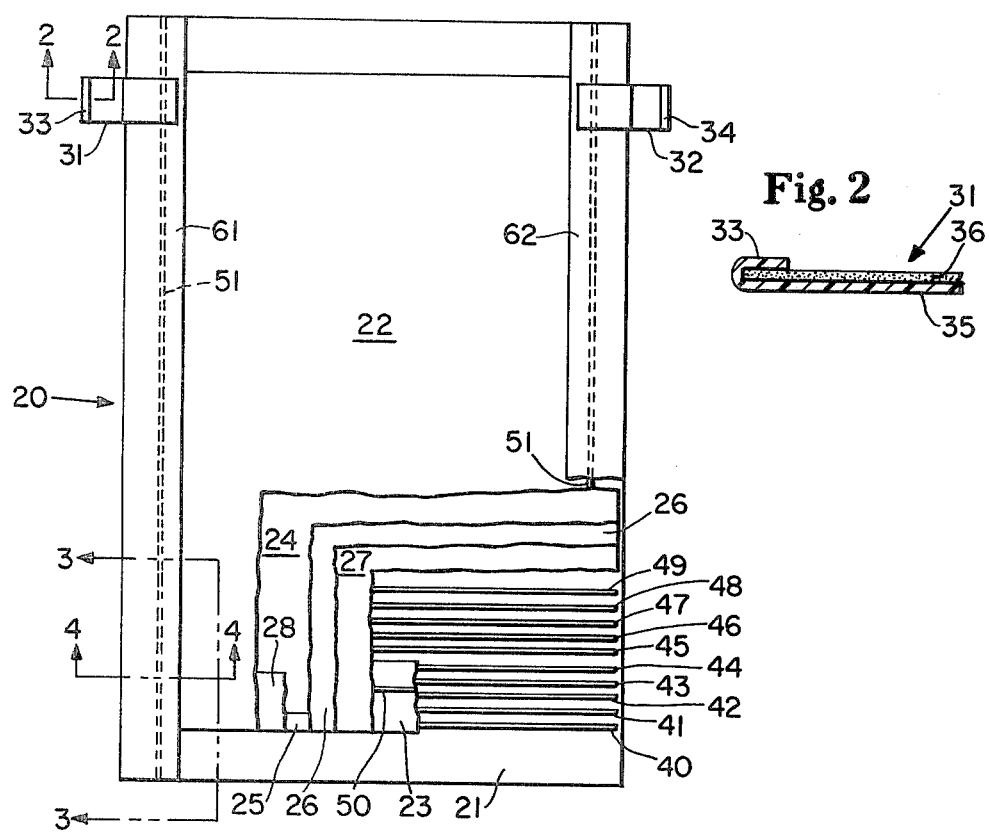
FIG. 1 is partially torn away plan view of a disposable diaper embodying the present invention.
Figure 2:
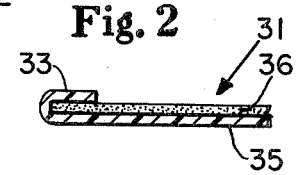
FIG. 2 is an enlarged scale fragmentary sectional view of a tape-tab fastener taken along line 2—2 of FIG. 1.
Figure 3:
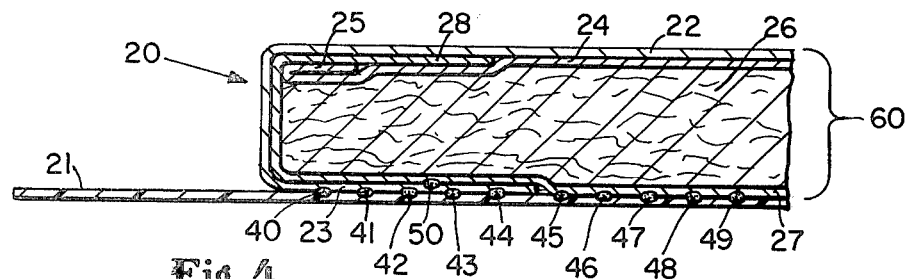
FIG. 3 is an enlarged scale, somewhat schematic fragmentary sectional view of the disposable diaper shown in FIG. 1 which view is taken along line 3—3 thereof.
Figure 4:
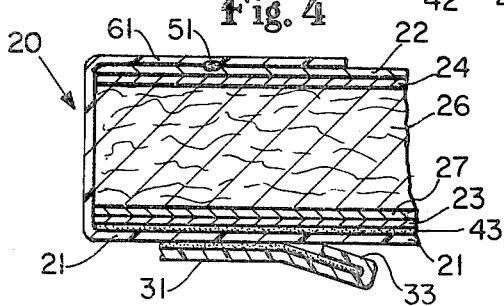
FIG. 4 is an enlarged scale, somewhat schematic fragmentary sectional view of the disposable diaper shown in FIG. 1 which view is taken along line 4—4 thereof, and in which view a sectional view of a tape-tab fastener similar to FIG. 2 is associated and disposed in a mother's bond position.
Figure 5:
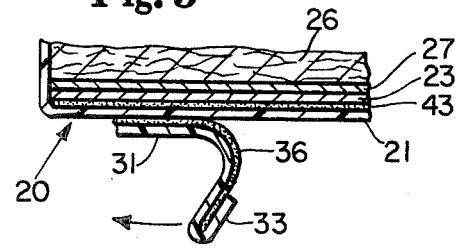
FIG. 5 is an enlarged scale view similar to FIG. 4 but which shows a fragmentary tape-tab fastener partially peeled from a front surface portion of the mother's bond region of the backsheet of a disposable diaper embodying the present invention.

An exemplary disposable diaper embodiment of the present invention is shown, partially torn away, in the plan view of FIG. 1 and the sectional views of FIGS. 3 and 4 to be diaper 20 comprising a backsheet 21, a topsheet 22 having a backwardly U-folded end edge portion 23, a front tissue sheet 24 having a forwardly U-folded end edge portion 25, an absorbent batt 26, a back tissue sheet 27 having a forwardly U-folded end edge portion 28, tape-tab fasteners 31 and 32 having mother's bond ends of a high tensile low elasticity substrate 35, FIG. 2, coated with a peelable adhesive 36 and having non-adhesively coated, distal end grasping portions 33 and 34 respectively, FIG. 1, and glue beads 40 through 51. A substantially similar diaper construction is disclosed in U.S. Pat. No. 3,952,745, which is hereby incorporated by reference, except the diaper construction disclosed in that patent does not have grasping portions 33 and 34, and does not have glue beads 41–44 and 46–49 inclusive, which are included in the present preferred embodiment diaper construction. As indicated on FIG. 3, the backsheet 21, topsheet 22, front tissue sheet 24, absorbent batt 26, and back tissue sheet 27 are grouped together and hereby designated pad assembly 60.

Briefly, the present invention provides a reinforced mother's bond region on a low tensile strength, highly elongatable backsheet of a disposable diaper which region is preferably large enough to enable the free ends of tape-tab fasteners to be secured anywhere on a wide abdominal portion of the diaper so that such diapers can be fitted to a range of sizes of users. Essentially, the reinforcement is provided by coating a predetermined surface area of the backsheet with a material such as a hot melt adhesive having relatively great tensile strength, and a relatively low elongation to tensile force property. The coating may be applied in a predetermined pattern and may adhesively secure the backsheet to the pad assembly of the diaper in the mother's bond region. This reinforced mother's bond region also provides, in combination with peelable-adhesive-coated tape-tab fasteners, mother's bonds having improved tensile strength, and which bonds can be peeled apart and refastened. That is, the reinforced mother's bond region of the backsheet resists stretching and tearing and results in improved tensile strength mother's bonds as well as rendering the mother's bonds peelable and refastenable.

The tensile strength property, and the elongation versus tensile force property relations of the reinforcing coating and/or adhesive material, the backsheet material, the topsheet material, and the back tissue sheet material of diaper 20 are believed to be significantly more relevant than their relative moduli of elasticity. That is, in use, diaper fasteners are subjected to tensile forces during use and, if peelable, to peeling forces while being released. Therefore, a suitable fastener and the diaper structure to which it is attached must have sufficient strength to withstand such forces. An exemplary backsheet material is substantially moisture impervious and, to conserve the usage of such material in disposable consumer products such as disposable diapers, it should be very thin; for example, one-half (0.5) mil or one (1.0) mil thick polyethylene. Whereas, polyethylene has a sufficiently great modulus of elasticity (i.e., the ratio of the increment of unit stress to increment of unit deformation within the elastic limit) to withstand normal ranges of diaper application forces if it has a sufficiently great cross sectional area to not be strained beyond its elastic limit, elongation versus tensile force more aptly relates to a material's capacity to withstand a force without undue stretching and tearing. Thus, the materials tensile data plotted in FIG. 6 is percent elongation versus tensile force per inch of width through the range of forces believed to be relevant to disposable diaper applications.

The backsheet 21, FIG. 1, is preferably comprised of an embossed polyethylene film having a melt index between about 1.5 and about 5.4, a density between about 0.917 and about 0.926 grams per cubic centimeter, an unembossed caliper of about one mil as measured under a load of approximately 95 grams per square inch, and an embossed caliper between about 3 and 3½ mils under the same loading. Curve 81, FIG. 6, is a plot of percent elongation versus tensile force per lineal inch of width which force is applied to a representative sample of such embossed polyethylene film. Such film is available from the Monsanto Company, St. Louis, Mo., and is deisgnated by Monsanto as No. 8020.

The topsheet 22 of diaper 20 may comprise a water pervious nonwoven, carded rayon which has been bonded with an acrylic latex and which has a nominal thickness of about 5 mils. Curve 82, FIG. 6, is a plot of percent elongation versus tensile force per lineal inch of width which force is applied to a representative sample of such a nonwoven rayon which is available from The Kendall Company, Walpole, Mass., and which is designated Webline No. F6211.

An alternative topsheet material is a water pervious nonwoven, carded polyester which has been bonded with an acrylic latex. Curve 85, FIG. 6, is a plot of percent elongation versus tensile force per lineal inch of width which force is applied to a representative sample of such a nonwoven polyester which is also available from The Kendall Company and designated SW 477.130.

The front and back tissue sheets 24 and 27, respectively, are preferably comprised of wet strength tissue paper having basis weights of about 14 and 12 pounds per 3,000 square feet, respectively. Curve 83, FIG. 6, is a plot of percent elongation versus tensile force per lineal inch of width which force is applied to a representative sample of a suitable back tissue sheet material. As indicated on FIG. 6, this material broke under a tensile force of about 500 grams per lineal inch of width at an elongation of about 12 percent.

Briefly, a preferred embodiment of diaper 20, FIG. 1, is assembled by first assembling pad assembly 60, FIG. 3, and then securing the outwardly facing surfaces of pad assembly 60 to the backsheet 21 with glue beads 40 through 49. Then, as best seen in FIG. 1, side edge portions 61 and 62 of backsheet 21 are U-folded forwardly about the side edges of the pad assembly and secured to the front surface of topsheet 22 by two glue beads 51. The diaper is completed by attaching the factory bond ends of tape-tab fasteners 31 and 32 to the rear corners of the diaper as indicated in FIG. 1.

Preferably, glue beads 40 through 44 and 46 through 49 are adhesive material having high tensile strength and a low elongation to tensile force property relative to the corresponding properties of backsheet 21. Such an adhesive which is suitable is National Starch No. 34-2933, a hot melt adhesive which is available from the National Starch and Chemical Corporation, Plainfield, N.J. Glue bead 45 can be the same adhesive for the purposes of the present invention but preferably is an adhesive material such as Eastobond No. A-3, a hot melt adhesive available from Eastman Chemical Products, Inc., Kingsport, Tenn. in order to concurrently provide the benefits of the invention claimed in U.S. Pat. No. 3,952,745 which has hereinbefore been incorporated herein by reference.

In a diaper 20, FIG. 1, wherein the pad assembly 60 is secured to the backsheet 21 by a plurality of generally parallel glue beads, namely glue beads 40 through 49 as shown in FIGS. 1 and 3, and which glue beads extend transverse virtually the entire width of the diaper, the mother's bond region is the area defined by the plurality of glue beads. Alternatively, the plurality of glue beads is designated an array of glue beads, or a predetermined pattern of glue or adhesive or coating material.

Curve 84, FIG. 6, is a plot of percent elongation versus tensile force per lineal inch applied to a representative sample of a mother's bond region of a disposable diaper 20 where the backsheet is the polyethylene associated with curve 81, FIG. 6; the topsheet is the rayon topsheet material associated with curve 82, FIG. 6; the back tissue sheet is the tissue paper associated with curve 83, FIG. 6; and the structure was bonded together with glue beads 41 through 45 of the hot melt, National Starch Adhesive No. 34-2933 described hereinbefore. It is apparent from curve 84 in view of curves 81 through 83 that the adhesive contributes greatly to the tensile strength of the structure, and its greatly reduced percent elongation versus tensile force property.

Diaper 20 is preferably applied to the torso of a user by placing the lower back torso portion of the user on the tab end of the diaper, and then U-folding the remainder of the diaper forwardly and upwardly so that it covers the crotch and abdominal regions of the user. The peelable-adhesive-coated tape-tab free ends are then fastened to the mother's bond region of the diaper which is then disposed across the abdominal region of the user. When thus applied the tape-tab fasteners apply tensile forces to both the rear portion of the diaper and to the mother's bond region of the diaper. The tensile forces applied to the mother's bond region are generally substantially parallel to the glue beads although it is not intended to thereby limit the present invention.

While the preferred embodiment disposable diaper 20 is described as having glue beads 40 through 49, FIGS. 1 and 3, it is not intended to thereby limit the invention to an array of ten glue beads. Rather, a plurality of such glue beads or other patterns of adhesive material or coating material are suitable for reinforcing the backsheet of disposable diapers embodying the present invention. While continuous coatings are not precluded from the present invention, preferred patterns of coatings and/or adhesives have composite areas of five (5) percent or greater of the mother's bond region; more preferably they have composite areas of from about five (5) percent to about twenty-five (25) percent; and, most preferably have composite areas of from about ten (10) to about fifteen (15) percent of the mother's bond region. That is, suitable backsheet material described hereinbefore can be sufficiently reinforced by coating substantially less than the full mother's bond region with suitable coating materials having the properties described hereinbefore whereby the usage of such coating materials can be conserved.

Glue beads 40 through 49, FIGS. 1 and 3, are preferably sufficiently closely spaced relative to the width of the mother's bond ends of the tape-tab fasteners that the widths of the tape-tab fasteners will span side-by-side segments of at least two beads and an intervening unsupported strip of the backsheet. Moreover, the glue beads are preferably from about three-quarters of one millimeter (0.75 mm) wide to about one-and-one-half millimeters (1.5 mm) wide and are nominally spaced about ten millimeters (10 mm) center-to-center in diapers wherein the mother's bond ends of the tape-tab fasteners are about sixty-five millimeters wide. It is, however, believed that the widths, spacing, and composite surface areas of glue beads and/or other patterns of coatings and/or adhesives may be varied depending on the properties of the backsheet material and the coating and/or adhesive materials.

An alternate disposable diaper embodying the present invention is the same as disposable diaper 20, FIGS. 1 through 5, except that the beads 41 through 44 and 46 through 49 are coated onto or applied to the backsheet as indicated in FIG. 1 but do not secure the backsheet to the pad assembly of the diaper. Rather, they simply coat a portion of the inwardly facing surface of the mother's bond region and reinforce it against stretching and tearing by virtue of the coating or bead material having relatively high tensile strength and having a relatively low elongation to tensile force property.

Yet another alternate embodiment of the present invention is the same as the alternate disposable diaper described just above except a reinforcing coating is applied to the outwardly facing surface of the mother's bond region. This coating may be continuous or applied in a pattern such as defined by, for example, glue beads 41 through 44 and 46 through 49, FIGS. 1 and 3.

While particular embodiments of the present invention have been illustrated and described, it would be obvious to those skilled in the art that various other changes and modifications can be made without departing from the spirit and scope of the invention. Therefore, it is intended to cover in the appended claims all such changes and modifications that are within the scope of this invention.

What is claimed is:

1. In an improved disposable diaper of the type having an absorbent pad assembly secured to a substantially moisture impervious backsheet of relatively thin material having a relatively high elongation to tensile force property, and having peelable adhesive coated tape-tab fasteners wherein at least one of said tape-tab fasteners has a nonadhesive coated distal end portion to provide a mother's grasping portion for facilitating removal of said diaper from a user, the improvement comprising a coating disposed on an inwardly facing surface of a mother's bond region of said backsheet, said coating comprising a self-adhering coating material having a relatively high tensile strength and a low elongation to tensile force property relative to said backsheet.

2. The improved disposable diaper of claim 1 wherein said coating material is disposed discontinuously on said mother's bond region, said coating material covering a composite area that is substantially less than the area of said mother's bond region.

3. The improved disposable diaper of claim 2 wherein said discontinuous coating material is applied in a predetermined pattern.

4. The improved disposable diaper of claim 3 wherein said pattern comprises a plurality of beads of said coating material.

5. The improved disposable diaper of claim 4 wherein said plurality of beads are disposed generally in parallel relation and extend transverse said mother's bond region.

6. The improved disposable diaper of claim 5 wherein said beads are sufficiently closely spaced relative to the width of said tape-tab fasteners that the width of each said tape-tab fastener will span side-by-side segments of at least two said beads and an intervening unsupported strip of said backsheet.

7. The improved disposable diaper of claim 6 wherein said beads are preferably from about three-quarters of one millimeter (0.75 mm) to about one-and-one-half-millimeters (1.5 mm) wide and are nominally spaced about ten millimeters (10 mm) center-to-center, said tape-tab fasteners have nominal widths of from about twenty millimeters (20 mm) to about thirty millimeters (30 mm), and said mother's bond region is nominally about sixty-five millimeters (65 mm) wide.

8. In an improved disposable diaper of the type having an absorbent pad assembly secured to a substantially moisture impervious backsheet of relatively thin material having a relatively high elongation to tensile force property, and having peelable adhesive coated tape-tab fasteners, the improvement comprising a coating disposed on an inwardly facing surface of a mother's bond region of said backsheet, said coating comprising a self-adhering coating material having a relatively high tensile strength and a low elongation to tensile force property relative to said backsheet.

9. The improved disposable diaper of claim 8 wherein said coating material is disposed discontinuously on said mother's bond region, said coating material covering a composite area that is substantially less than the area of said mother's bond region.

10. The improved disposable diaper of claim 9 wherein said discontinuous coating material is applied in a predetermined pattern.

11. The improved disposable diaper of claim 10 wherein said pattern comprises a plurality of beads of said coating material.

12. The improved disposable diaper of claim 11 wherein said plurality of beads are disposed generally in parallel relation and extend transverse said mother's bond region.

13. The improved disposable diaper of claim 12 wherein said beads are sufficiently closely spaced relative to the width of said tape-tab fasteners that the width of each said tape-tab fastener will span side-by-side segments of at least two said beads and an intervening unsupported strip of said backsheet.

14. The improved disposable diaper of claim 13 wherein said beads are preferably from about three-quarters of one millimeter (0.75 mm) to about one-and-one-half-millimeters (1.5 mm) wide and are nominally spaced about ten millimeters (10 mm) center-to-center, said tape-tab fasteners have nominal widths of from about twenty millimeters (20 mm) to about thirty millimeters (30 mm), and said mother's bond region is nominally about sixty-five millimeters (65 mm) wide.

15. The improved disposable diaper as recited in claims 1, 2, 3, 4, 5, 7, 8, 9, 10, 11, 12, 13, or 14 wherein said coating material is an adhesive material and secures said mother's bond region of said backsheet to a juxtaposed surface area of said absorbent pad assembly.

16. The improved disposable diaper of claim 15 wherein said composite area of said adhesive material is greater than about five percent (5%) of the area of said mother's bond region.

17. The improved disposable diaper of claim 15 wherein said composite area of said adhesive material is from about five (5) to about twenty-five (25) percent of the area of said mother's bond region.

18. The improved disposable diaper of claim 15 wherein said composite area of said adhesive material is from about ten (10) to about fifteen (15) percent of said mother's bond region.

19. The improved disposable diaper of claim 15 wherein a substantial portion of said juxtaposed surface area of said pad assembly is an outwardly facing surface area of a flexible sheet member of said pad assembly, said flexible sheet member comprising material having an elongation to tensile force property which is generally comparable to that property of said backsheet.

* * * * *